(12) United States Patent
Morcher

(10) Patent No.: US 6,740,116 B2
(45) Date of Patent: May 25, 2004

(54) INTRAOCULAR LENS

(75) Inventor: Olaf Morcher, Stuttgart (DE)

(73) Assignee: Morcher GmbH, Stuttgart (DE)

( * ) Notice: Subject to any disclaimer, the term of this patent is extended or adjusted under 35 U.S.C. 154(b) by 0 days.

(21) Appl. No.: 10/148,117

(22) PCT Filed: Jan. 31, 2001

(86) PCT No.: PCT/DE01/00402

§ 371 (c)(1),
(2), (4) Date: May 24, 2002

(87) PCT Pub. No.: WO01/66040

PCT Pub. Date: Sep. 13, 2001

(65) Prior Publication Data

US 2002/0183842 A1 Dec. 5, 2002

(30) Foreign Application Priority Data

Mar. 4, 2000 (DE) .......................... 100 10 683

(51) Int. Cl.⁷ .............. A61F 2/14; A61F 2/16
(52) U.S. Cl. ....................... 623/4.1; 623/6.17
(58) Field of Search ............... 623/4.1, 6.17, 623/6.48, 6.32, 6.33

(56) References Cited

U.S. PATENT DOCUMENTS

| | | | | |
|---|---|---|---|---|
| 4,655,774 A | * | 4/1987 | Choyce ................ | 623/5.11 |
| 4,955,904 A | | 9/1990 | Atebara et al. | |
| 4,976,732 A | * | 12/1990 | Vorosmarthy .......... | 623/6.17 |
| 5,098,444 A | * | 3/1992 | Feaster .............. | 623/6.36 |
| 5,662,706 A | * | 9/1997 | Legerton et al. ...... | 623/5.13 |
| 6,221,106 B1 | * | 4/2001 | Hermeking ............ | 623/6.4 |
| 6,280,469 B1 | * | 8/2001 | Terry et al. ......... | 623/4.1 |

FOREIGN PATENT DOCUMENTS

| | | |
|---|---|---|
| DE | 3926536 | 2/1991 |
| FR | 2696340 | 4/1994 |
| WO | 0067677 | 11/2000 |

* cited by examiner

Primary Examiner—David H. Willse
Assistant Examiner—Suzette J. Jackson
(74) Attorney, Agent, or Firm—Collard & Roe, P.C.

(57) ABSTRACT

A foldable intraocular lens with an iris diaphragm (2) for covering an aniridia. The iris diaphragm can thus be based upon a natural iris. The diaphragm essentially comprises a film, printed with a pigment, provided with a sealing layers and completely embedded in the transparent lens material.

9 Claims, 1 Drawing Sheet

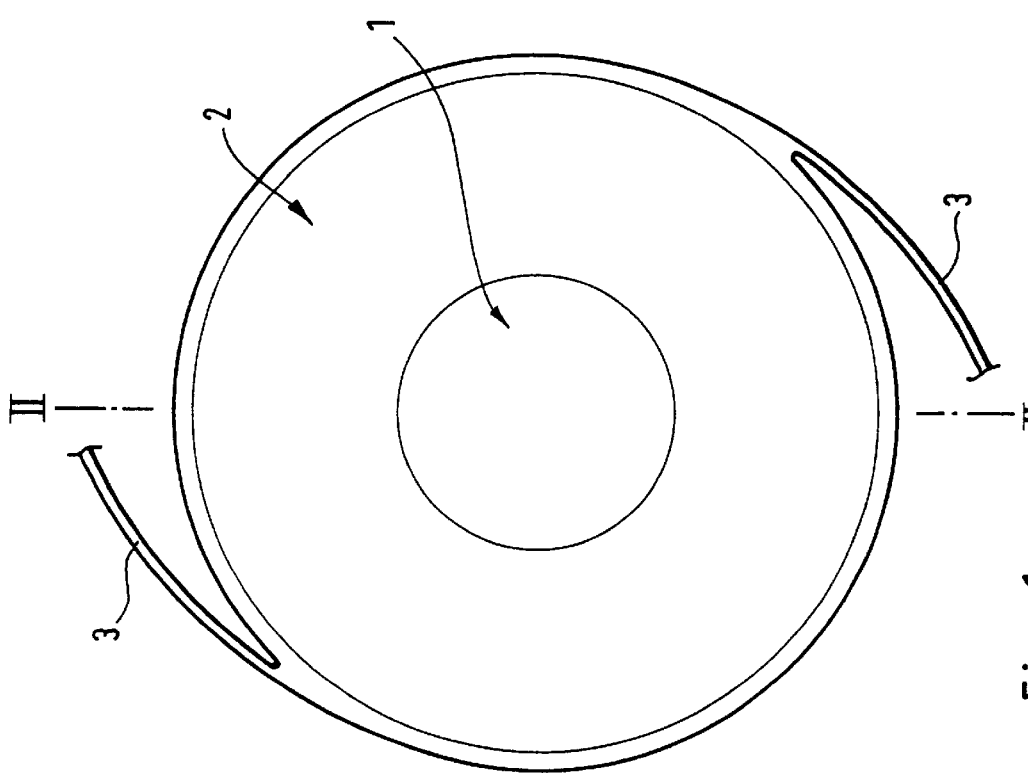

INTRAOCULAR LENS

CROSS REFERENCE TO RELATED APPLICATIONS

Applicant claims priority under 35 U.S.C. §119 of GERMAN Application No. 100 10 683.8 filed on Mar. 4, 2000. Applicant also claims priority under 35 U.S.C. §120 of PCT/DE01/00402 filed on Jan. 31, 2001. The international application under PCT article 21(2) was not published in English.

This invention relates to an intraocular lens with a transparent central area and an iris diaphragm adjacent to it radially for correcting or covering an aniridia.

Eye injuries often lead to injury to the iris, so there is a comparatively high demand for intraocular lenses with iris diaphragms.

Such lenses available on the market today have a two-part design with a diaphragm of black polymethyl methacrylate designed like a ring. A lens of transparent polymethyl methacrylate is secured or held mechanically in the opening in the diaphragm.

These lenses have proven successful in practice.

However, since these lenses have a comparatively limited flexibility, a relatively large surgical opening must be created for implantation of the lens in the eye, so that healing of the eye takes a relatively long time.

In addition, it is also desirable for the optical appearance of the diaphragm of the implanted lens to approximate even more closely the natural iris. However, it is extremely cost-intensive to use differently colored materials for the iris diaphragms with these known lenses. If instead of this, a pigment is applied to the black iris diaphragm, e.g., by painting or printing, there may be toxicological risks or problems with regard to long-term stability.

U.S. Pat. Nos. 4,955,904 and 5,622,706 disclose masked intraocular lenses, where the masking serves to correct imaging defects of the eye, not to replace an iris. According to U.S. Pat. No. 4,955,904, pigments which serve to form the mask may be embedded in the lens.

The object of this invention is to create an improved lens for treatment of aniridia. unit, whereby the diaphragm consists essentially of an opaquely pigmented film which is embedded in an outer area which is connected in one piece to the central area of the lens and is completely sheathed by transparent lens material.

The object is achieved according to this invention by the fact that the lens and the diaphragm are designed as a one-piece unit, whereby the diaphragm consists essentially of a flexible, opaquely pigmented film which is embedded in an outer area which is connected in one piece to the central area of the lens and is completely sheathed by transparent lens material, and where the multi-layer film has an inner pigment carrier layer and a barrier layer which completely seals and encloses the pigment carrier layer—even at the edges of the layer—and is resistant to diffusion of the pigments.

According to an especially preferred embodiment of this invention, the film may be designed in multiple layers and may have an inner pigment carrier layer, which can preferably be designed to be colored by printing technology, and a barrier layer which seals and sheaths the pigment carrier layer completely—even at the edges of the layer—and makes it resistant to diffusion of the pigments.

In this embodiment, the transparent lens material enclosing the multi-layer film serves primarily only to guarantee a good biological tolerability of the lens in the eye, while the barrier layer on the film is responsible for sealing the pigments.

In addition, this embodiment offers the special advantage that conventional water-absorbent hydrophilic materials which are conventionally used for foldable (soft) lenses can readily be used as the transparent lens material, so that a foldable intraocular aniridia lens can now be produced for the first time.

A copolymer of methyl methacrylate and 2-hydroxyethyl methacrylate is preferably used as the transparent lens material. This material optimizes the foldability and water retention of the lens during surgical implantation in the eye and at the same time ensures the long-term stability in the biological medium as well as the optical quality. In addition, this material is heat-resistant and is suitable for sterilization with steam.

In particular, if the lens material is highly hydrophilic and absorbs water, the barrier layer should preferably consist of a hydrophobic material, e.g., silicone. Thus, diffusion of pigments can be reliably prevented. In addition, silicone also remains stable even in steam sterilization of the lens.

The primary carrier film is preferably made of a heat-resistant material suitable for the desirable steam sterilization of the lens, such as polypropylene and/or polyimide in particular, and is printed with a colored pattern corresponding to that of a natural iris, e.g., by screen printing.

In addition, with regard to preferred features of this invention, reference is made to the claims as well as the following description of the drawings, on the basis of which the especially preferred embodiment of the lens according to this invention and its production are described in greater detail.

The drawings show:

FIG. 1 a top view of the lens according to this invention,

FIG. 2 a sectional view according to sectional line II—II in FIG. 1, and

FIG. 3 a sectional view of a modified embodiment according to FIG. 2.

The intraocular lens illustrated in FIGS. 1 and 2 has a lens-shaped transparent central area 1, which is connected to an opaque, essentially ring-shaped iris diaphragm 2 on the outside radially. This iris diaphragm consists essentially of a ring-shaped thin film 2' which is designed in the manner of an iris due to pigments printed on it and is practically opaque. This iris-like primary carrier film 2' is sheathed with a barrier layer 2" which is also closed at the edges of the primary carrier film 2'.

The entire iris diaphragm 2 is embedded in the transparent material of the central area 1, i.e., the central area 1 is continued toward the outside radially in a sheathing 1' in which the iris diaphragm 2 is embedded and whose outer edge encloses the outer edge of the iris diaphragm 2.

In addition, haptic elements 3 may be molded onto the outer edge of the sheathing 1', developing into the sheathing 1' in one piece and being made of the same transparent material.

The primary carrier film 2' is preferably made of polypropylene and/or polyimide. The sealing 2" is preferably made of silicone, and the central area 1 and the sheathing 1' are preferably made of a copolymer of methyl methacrylate and 2-hydroxymethyl methacrylate.

The lens of FIGS. 1 and 2 can be produced by first printing the primary carrier film 2' with pigments according to the pattern of a natural iris and punching out a ring shape corresponding to an iris.

Then this finished primary carrier film 2' is sealed with the barrier layer 2".

The iris diaphragm 2 produced in this way is then encased in a copolymer of methyl methacrylate and 2-hydroxymethyl methacrylate, so that after the cast material hardens it is in the form of a thick blank which projects axially and radially well beyond the iris diaphragm 2.

The lens with haptic elements 3 as illustrated in FIGS. 1 and 2 is then produced by machining the blank.

The finished lens is then subjected to steam sterilization and placed in a sterile salt water bath. In this way, a very flexible, foldable lens which retains water is created. This lens can be implanted in the eye through a small surgical opening.

FIG. 3 shows as an example that, in deviation from the illustration in FIG. 2, the lens may also have a curved shape.

In addition, the biconvex design of the central area 1 of the lenses shown in FIGS. 2 and 3 is given only as an example. If needed, a plano-convex or convex-concave design is also possible.

In addition, the outside edge of the sheathing 1' may also be designed as a bead having in principle any desired bead cross sections, if this is medically desirable.

The shape of the haptic elements 3 illustrated here is also intended only as an example. Other shapes, e.g., according to medical specifications, are readily possible. For example, the haptic elements 3 may also be in the shape of eyelets.

What is claimed is:

1. An intraocular lens having a transparent central area (1) as well as an iris diaphragm (2) connected thereto on the outside radially to correct or cover an aniridia, wherein the lens and diaphragm (2) are designed as a one-piece unit and the diaphragm consists essentially of a flexible, opague, pigmented film (2', 2") which is embedded in a lens outer area (1') that is connected in one piece to the central area (1) of the lens and is completely sheathed by the transparent lens material, and wherein the film has multi-layers including an inner pigment carrier layer (2') and a barrier layer (2") which completely sheaths and seals the pigment carrier layer—even at the edges of the layer—and is resistant to diffusion of the pigments.

2. The lens according to claim 1, characterized in that the transparent lens material is hydrophilic and the material of the barrier layer (2") is hydrophobic.

3. The lens according to claim 1, characterized in that the pigment carrier layer is made of a film (2') which is printed in color.

4. The lens according to claim 1, characterized in that the central area (1) of the lens is arranged with an axial offset relative to the plane of the iris diaphragm (2).

5. The lens according to claim 1, characterized in that the transparent lens material is a copolymer of methyl methacrylate and 2-hydroxymethyl methacrylate.

6. The lens according to claim 1, characterized in that the film (2') is made of polypropylene and/or polyimide.

7. The lens according to claim 1, characterized in that the barrier layer (2") is made of silicone.

8. A method of producing a lens according to claim 1, characterized in that to produce an iris diaphragm (2), a film (2') is printed with pigments and punched out according to a natural iris and then is provided with a seal (2") by encasing the punched-out film in transparent lens material, and a blank obtained after curing the lens material is machined according to the desired lens shape.

9. The method according to claim 8, characterized in that a film (2') which is used to produce the iris diaphragm (2) is pigmented by screen printing.

* * * * *